United States Patent [19]

Loscalzo

[11] Patent Number: 5,002,964

[45] Date of Patent: Mar. 26, 1991

[54] S-NITROSOCAPTOPRIL COMPOUNDS AND THE USE THEREOF

[75] Inventor: Joseph Loscalzo, Dedham, Mass.

[73] Assignee: Brigham & Women's Hospital, Boston, Mass.

[21] Appl. No.: 206,763

[22] Filed: Jun. 15, 1988

[51] Int. Cl.$^5$ .................. A61K 31/40; C07D 207/09; C07D 207/12

[52] U.S. Cl. .................... 514/423; 546/226; 546/242; 546/245; 548/533; 548/537; 548/952; 548/953; 560/16; 560/147; 562/426; 562/556; 564/154

[58] Field of Search ............... 548/533, 537; 514/423

[56] References Cited

U.S. PATENT DOCUMENTS

| | | | |
|---|---|---|---|
| 4,046,889 | 9/1977 | Ondetti et al. | 424/244 |
| 4,052,511 | 10/1977 | Cushman et al. | 424/274 |
| 4,053,651 | 10/1977 | Ondetti et al. | 548/342 X |
| 4,113,715 | 9/1978 | Ondetti et al. | 424/177 X |
| 4,129,571 | 12/1978 | Ondetti et al. | 546/188 X |
| 4,154,840 | 5/1979 | Ondetti et al. | 546/118 X |
| 4,154,960 | 5/1979 | Ondetti et al. | 562/436 |
| 4,692,458 | 9/1987 | Ryan et al. | 514/362 |

OTHER PUBLICATIONS

Sieh, D. H. et al., *J. Pharm. Sci.* 73:1545–1547 (1984).
Loscalzo, J. *J. Clin. Invest.* 76:703–708 (1985).
Ignarro, L. J. et al., *Biochim. Biophys. Acta* 631:221–231, (1980).
Horowitz, J. D. et al., *Circulation* 68:1247–1253, (1983).
Cushman, D. W. et al., *Biochemistry* 16:5484–5491, (1977).
Kadin, H. in *Analytical Profiles of Drug Substances* 11:79–137, Academic Press, NY (1982).
Lidell, H. et al., *Analyst* 84:188–190, (1959).
van Gilst, W. H. et al., *J. Cardiovasc. Pharmacol.* 9:254–255, (1987).
van Gilst, W. H. et al., *Circ. Suppl. II*, 78:II-221, (Abstr. 0882) (1988), abstract considered.

*Primary Examiner*—Joseph Paul Brust

*Attorney, Agent, or Firm*—Sterne, Kessler, Goldstein & Fox

[57] ABSTRACT

The invention relates to novel nitroso compounds having the formula:

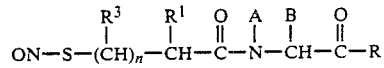

wherein,

R is hydroxy, $NH_2$, $NHR^4$, $NR^4R^5$ or $C_1$–$C_7$ alkoxy, wherein $R^4$ and $R^5$ are $C_1$–$C_4$ alkyl, aryl, or $C_1$–$C_4$ alkyl substituted by aryl;

$R^1$ is hydrogen, $C_1$–$C_7$ alkyl or $C_1$–$C_7$ alkyl substituted by phenyl, amino, guanidino, $NHR^6$ or $NR^6R^7$, wherein $R^6$ and $R^7$ are methyl, or $C_1$–$C_4$ acyl;

$R^3$ is hydrogen, $C_1$–$C_7$ alkyl or $C_1$–$C_7$ alkyl substituted by phenyl;

n is 0 to 2;

A is hydrogen,
  lower $C_1$–$C_7$ alkyl,
  lower $C_2$–$C_7$ alkylene,
  lower $C_2$–$C_7$ alkylene substituted by hydroxy, $C_1$–$C_4$ alkyl, aryl, or
  a $C_4$–$C_7$ ring which may be fused to a benzene ring;

B is hyrogen,
  lower $C_1$–$C_7$ alkyl,
  phenyl,
  lower $C_1$–$C_7$ substituted by phenyl, hydroxy, guanidino, amino, imidazoyl, indolyl, mercapto, mercapto substituted by lower $C_1$–$C_4$ alkyl, carbamoyl, or carboxyl, or
  lower $C_2$–$C_7$ alkylene.

The invention also relates to compounds having the following formula:

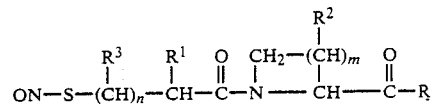

wherein R, $R^1$, $R^3$ and n are as defined above; $R^2$ is (Abstract continued on next page.)

hydrogen, hydroxy, $C_1$–$C_4$ alkoxy, aryloxy or $C_1$–$C_7$ alkyl; and m is 1 to 3.

The invention also relates to pharmaceutical compositions comprising the nitrosothiol compounds of the invention together with a pharmaceutically acceptable carrier.

The invention also relates to methods for treating acute myocardial infarction, left ventricular dysfunction without overt heat failure, hypertension, pulmonary hypertension, congestive heart failure, angina pectoris, vascular thrombosis, Raynauds syndrome, Scleroderma, toxemia of pregnancy, acute renal failure, diabetic nephropathy, and renal artery stenosis, and to methods of inhibiting ACE and effecting vasodilation comprising administering the nitrosothiol compounds of the invention to an animal.

17 Claims, 5 Drawing Sheets

S-NITROSOCAPTOPRIL COMPOUNDS AND THE USE THEREOF

FIELD OF THE INVENTION

This invention relates to new pharmaceutical preparations and the use thereof for the treatment of acute myocardial infarction, left ventricular dysfunction without overt heart failure, congestive chart failure, angina pectoris, vascular thrombosis, hypertension, Raynauds syndrome, scleroderma, toxemia of pregnancy, acute renal failure, diabetic nephropathy, renal artery stenosis, and pulmonary hypertension. The invention also related to methods for inhibiting ACE and effecting vasodilation by administering the pharmaceutical preparations of the invention to an animal.

BACKGROUND OF THE INVENTION

A variety of vasodilators currently exist for the treatment of hypertensive states, angina pectoris, and congestive heart failure. These agents may be classified according to their primary mechanism of action. Two important groups of these agents are the angiotensin converting enzyme inhibitors (useful in hypertension and congestive heart failure, but not angina) and nitrates (useful in angina and congestive heart failure, but less effective in hypertension). Neither of these groups are believed to be clinically important as antiplatelet agents.

Angiotensin converting enzyme (ACE) is capable of converting angiotensin I to angiotensin II by removal of the carboxy terminal His-Leu. Angiotensin I is formed by the action of the enzyme renin and endopeptidase found in the kidney, other tissues, and plasma. Blood pressure is affected by various peptides found in the blood including angiotensin II. Angiotensin II is reported to be a powerful pressor agent found at elevated concentrations in the blood of patients with renal hypertension.

The level of ACE activity is ordinarily in excess, in both normal and hypertensive patients, of the amount needed to maintain observed levels of angiotensin II. However, it has been found that significant blood pressure lowering is achieved in hypertensive patients by treatment with ACE inhibitors (Gavras, I., et al., *New Engl. J. Med.* 291:817 (1974)). The role of ACE in the pathogenesis of hypertension has prompted a search for inhibitors of the enzyme that could act as antihypertensive drugs. A highly effective inhibitor, with high biological activity when orally administered, is D-3-mercapto-2-methylpropanoyl-L-proline, also known as captopril. Ondetti et al., U.S. Pat. No. 4,046,889 (1977); Cushman, D. W., et al., *Biochemistry* 16:5484 (1977); and Ondetti, M., et al., *Science* 196:441 (1977).

Captopril is believed to act by binding to the ACE active site. In early studies, the active site was postulated to be cationic and binding for the carboxyl end group of the substrate in a pocket or cleft. This pocket was believed to be capable of binding the side chain of the C-terminal amino acid and providing especially tight binding for the heterocyclic ring of a terminal proline residue. A similar pocket for the penultimate amino acid residue was postulated. The published data suggested a rather stringent steric requirement, since the D-form of the inhibitor was substantially more potent than its stereoisomer or the 3-methyl and unsubstituted analogs. The sulfhydryl group on the inhibitor, postulated to be bound at the active site near the catalytic center, was believed to play a central role in inactivation of the enzyme by combining with the zinc moiety known to be essential for catalytic activity. Substituents on the sulfhydryl, such as the methyl group, and an S-acetyl derivative, reportedly reduce the potency of the inhibitor. See Ryan et al., U.S. Pat. No. 4,692,458 (1987); and Cushman, D. W., et al., *Biochemistry*, supra.

In an effort to increase the stability and potency of captopril, a number of analogs have been prepared See, for example, Ondetti et al., U.S. Pat. Nos. 4,046,889 (1977), 4,052,511, 4,053,651, 4,113,751, 4,154,840, 4,129,571 (1978), and 4,154,960 (1979); Taub, U.S. Pat. No. 4,626,545 (1986); and Ryan et al., U.S. Pat. No. 4,692,458 (1987).

In contrast to ACE inhibitors, organic nitrate vasodilators (of which nitroglycerin is the prototypic compound) are direct smooth muscle relaxants that likely act by activating guanylate cyclase. These compounds are believed to be metabolized intracellularly to active intermediate forms, S-nitrosothiols, that in turn transfer the active nitrous oxide moiety to the heme activator site of guanylate cyclase and, thereby, lead to increased production of cyclic GMP and attendant smooth muscle relaxation. As with the ACE inhibitors, organic nitrates do not act on any specific regional arterial bed with selectivity, all beds being dilated relatively equivalently. Ignarro, L. J., et al., *Biochem. Biophys. Acta* 631:221-231 (1980). The authors showed that the S-nitrosothiols of cysteine, penicillamine, glutathione, and dithiothreitol are capable of activating soluble guanylate cyclase. The authors suggest that S-nitrosothiols could act as intermediates in the activation of guanylate cyclase by glycerol trinitrate, $NaNO_2$, and possibly nitroprusside.

Horowitz, J. D., et al., *Circulation* 68:1247-1253 (1983), disclose that the vasodilator action of nitroglycerin is closely linked to the availability of critical SH groups in vascular smooth muscle. The authors postulate that the activity of nitroglycerin is modulated through the formation of S-nitrosothiol compounds, which are formed by the interaction of nitroglycerin with tissue sulfhydryl groups. In fact, tolerance commonly develops to organic nitrates. This is believed to be a result of depletion of critical tissue sulfhydryl compounds, the exact chemical nature of which remains to be identified. Among the S-nitrosothiols disclosed to be potent activators of guanylate cyclase in arterial smooth muscle were the S-nitroso derivatives of cysteine, dithiothreitol, penicillamine, and reduced glutathione. Ascorbate was found to be totally ineffective.

Loscalzo, J., et al., *J. Clin, Invest.* 76:703-708 (1985), disclose the preparation of S-nitroso-N-acetyl cysteine. This compound is reported to be an extremely potent inhibitor of platelet aggregation.

Reports concerning development of pharmaceutical agents that lower blood pressure, improve congestive heart failure, or hasten resolution of anginal episodes notwithstanding, a need continues to exist for medicants that are useful in the treatment of these disorders particularly if they are shown to exhibit the following properties: (1) the agent should have a prompt onset of action and a lengthy duration of action; (2) the use of the agent should not be associated with the development of the tolerant state; (3) the agent should ideally be relatively coronary selective; (4) the agent should be equally useful in the treatment of all three of these disorders since they commonly occur in the same patient—i.e., the hypertensive patient with coronary artery disease manifesting as angina pectoris and chronic congestive heart failure; and (5) since platelets are important in the pathophysiology of ischemic heart disease states like angina pectoris, antiplatelet effects would be a very useful additional property.

SUMMARY OF THE INVENTION

The invention relates to compounds of the formula wherein
R is hydroxy, $NH_2$, $NHR^4$, $NR^4R^5$ or $C_1$-$C_7$ alkoxy, wherein $R^4$ and $R^5$ are $C_1$-$C_4$ alkyl, aryl, or $C_1$-$C_4$ alkyl substituted by aryl;

$R^1$ is hydrogen, $C_1$-$C_7$ alkyl or $C_1$-$C_7$ alkyl substituted by phenyl, amino, guanidino, $NHR^6$ or $NR^6R^7$, wherein $R^6$ and $R^7$ are methyl, or $C_1$-$C_4$ acyl;

$R^3$ is hydrogen, $C_1$-$C_7$ alkyl or $C_1$-$C_7$ alkyl substituted by phenyl;

n is 0 to 2;
A is hydrogen,
lower $C_1$-$C_7$ alkyl,
lower $C_2$-$C_7$ alkylene,
lower $C_2$-$C_7$ alkylene substituted by hydroxy, $C_1$-$C_4$ alkyl, aryl, or
a $C_4$-$C_7$ ring which may be fused to a benzene ring;
B is hydrogen,
lower $C_1$-$C_7$ alkyl, phenyl,
lower $C_1$-$C_7$ alkyl substituted by phenyl, hydroxy, guanidino, amino, imidazoyl, indolyl, mercapto, mercapto substituted by lower $C_1$-$C_4$ alkyl, carbamoyl, or carboxy, or
lower $C_2$-$C_7$ alkylene.

The invention also relates to compounds having the following formula:

wherein R, $R^1$, $R^3$ and n are as defined above; $R^2$ is hydrogen, hydroxy, $C_1$-$C_4$ alkoxy, aryloxy or $C_1$-$C_4$ alkyl; and m is 1 to 3.

The invention also relates to a pharmaceutical composition containing the compounds of the invention together with a pharmaceutically acceptable carrier.

The invention also relates to the administration of the pharmaceutical compositions of the invention to an animal for the treatment of acute myocardial infarction, left ventricular dysfunction without overt heart failure, congestive heart failure, angina pectoris, vascular thrombosis, hypertension, Raynauds syndrome, scleroderma, toxemia of pregnancy, acute renal failure, diabetic nephropathy, renal artery stenosis, and pulmonary hypertension.

The invention also relates to methods for inhibiting ACE and effecting vasodilation and platelet inhibition by administering the pharmaceutical compositions of the invention to an animal.

Despite the report of Cushman, D. W., et al., *Biochemistry, supra*, derivatization of the sulfhydryl group on captopril with the nitrous radical gives rise to a compound that retains the ability to inhibit ACE, and at the same time, has direct vasodilatory properties and inhibits platelet aggregation.

DESCRIPTION OF THE PREFERRED EMBODIMENTS

The invention relates to compounds of the formula (I):

wherein
R is hydroxy, $NH_2$, $NHR^4$, $NR^4R^5$ or $C_1$-$C_7$ alkoxy, wherein $R^4$ and $R^5$ are $C_1$-$C_4$ alkyl, aryl, or $C_1$-$C_4$ alkyl substituted by aryl;

$R^1$ is hydrogen, $C_1$-$C_7$ alkyl or $C_1$-$C_7$ alkyl substituted by phenyl, amino, guanidino, $NHR^6$ or $NR^6R^7$, wherein $R^6$ and $R^7$ are methyl, or $C_1$-$C_4$ acyl;

$R^3$ is hydrogen, $C_1$-$C_7$ alkyl or $C_1$-$C_7$ alkyl substituted by phenyl;

n is 0 to 2;
A is hydrogen,
lower $C_1$-$C_7$ alkyl,
lower $C_2$-$C_7$ alkylene,
lower $C_2$-$C_7$ alkylene substituted by hydroxy, $C_1$-$C_4$ alkyl, aryl, or
a $C_4$-$C_7$ ring which may be fused to a benzene ring;
B is hydrogen,
lower $C_1$-$C_7$ alkyl,
phenyl,
lower $C_1$-$C_7$ alkyl substituted by phenyl, hydroxy, guanidino, amino, imidazoyl, indolyl, mercapto, mercapto substituted by lower $C_1$-$C_4$ alkyl, carbamoyl, or carboxy, or
lower $C_2$-$C_7$ alkylene.

Preferred nitrosothiols have the formula (II):

wherein R, $R^1$, $R^3$ and n are as defined above; $R^2$ is hydrogen, hydroxy, $C_1$-$C_4$ alkoxy, aryloxy or $C_1$-$C_7$ alkyl; and m is 1 to 3.

By the term "animal" is meant all animals that may experience the beneficial effects of the invention. Foremost among such animals are humans; however, the invention is not intended to be so limiting.

The formulae above represents compounds having up to four asymmetric centers (represented by *). It is to be understood that the compounds of the invention may exist in stereosomeric, racemic, or diastereomeric forms. However, compounds derived from L-proline and its derivatives are preferred.

By the term "pharmaceutically acceptable salts" is intended compounds of the invention wherein R equals hydroxy together with a pharmaceutically acceptable base such as alkali or alkaline earth metal hydroxides, ammonium hydroxides, alkyl ammonium hydroxides, etc.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

Preferred proline nitrosothiol derivatives of the invention include:

S-nitrosocaptopril,
N-acetyl-S-nitroso-D-cysteinyl-L-proline,
N-acetyl-S-nitroso-D,L-cysteinyl-L-proline,
1-(4-amino-2-(S-nitroso)mercaptomethylbutanoyl)-L-proline,
1-[2-(S-nitroso)mercaptomethyl-6-(N-methyl-N-acetyl-amino)-hexanoyl]-L-proline,
1-[5-guanidino-2-(S-nitroso)mercaptomethylpentanoyl]-L-proline,
1-[5-amino-2-(S-nitroso)mercaptomethylpentanoyl]-4-hydroxy-L-proline,
1-[5-guanidino-2-(S-nitroso)mercaptomethylpentanoyl]-4-hydroxy-L-proline,
1-[2-aminomethyl-3-(S-nitroso)mercaptomethylpentanoyl]-L-proline and
S-nitroso-L-cysteinyl-L-proline.

An especially preferred proline nitrosothiol derivative is S-nitrosocaptopril.

Preferred non-proline nitrosothiol derivatives include:

N-[5-amino-2-(S-nitroso)mercaptomethylpentanoyl]glycine,
N-[5-amino-2-(S-nitroso)mercaptomethylpentanoyl]-L-leucine,
N-5-amino-2-(S-nitroso)mercaptomethylpentanoyl]-L-phenylalanine,
N-5-amino-2-(S-nitroso)mercaptomethylpentanoyl]-L-serine,
1-5-amino-2-(S-nitroso)mercaptomethylpentanoyl]-pipecolic acid,
Na-5-amino-2-(S-nitroso)mercaptomethylpentanoyl]-L-arginine,
Na[5-amino-2-(S-nitroso)mercaptomethylpentanoyl]-L-lysine,
Na[5-amino-2-(S-nitroso)mercaptomethylpentanoyl]-L-histidine,
N-[5-amino-2-(S-nitroso)mercaptomethylpentanoyl]-L-methionine,
N-5-amino-2-(S-nitroso)mercaptomethylpentanoyl]-L-tryptophan,
N-5-amino-2-(S-nitroso)mercaptomethylpentanoyl]-L-glutamine,
N-2-5-amino-(S-nitroso)mercaptomethylpentanoyl]-L-aspartic acid,
D-(S-nitroso)cysteinyl-L-alanine,
D-(S-nitroso)cysteinyl-L-threonine,
N-[5-guanidino-2-(S-nitroso)mercaptomethylpentanoyl]-L-leucine, and
1-[5-guanidino-2-(S-nitroso)mercaptomethylpentanoyl]pipecolic acid.

The S-nitroso derivatives of the invention have the unique property of inhibiting ACE and, at the same time, causing direct vasodilation and platelet inhibition. A molecule with all three of these properties is unique. Captopril, the prototype ACE inhibitor, does not produce direct vasodilation, nor does it inhibit platelet function. Captopril does lower blood pressure, but does so solely by virtue of direct inhibition of the synthesis of angiotensin II from angiotensin I via ACE.

Two important properties of this class of compounds are the direct vasodilatory action and platelet inhibiting action. Although the inventors do not intend to be bound by any particular theory, the vasodilation and platelet inhibiting actions appear to be the result of the nitrosothiol moiety of the molecule While a variety of nitrosothiols have been shown to be potent vasodilators and inhibitors of platelet aggregation (Loscalzo, J., et al., *J. Clin. Invest.* 76:703–708 (1985)), no other compound has been shown to be a potent vasodilator and inhibitor of platelet aggregation together with the property of being an ACE inhibitor. The two mechanisms of action of the compounds of the present invention--direct vasodilation and ACE inhibition--interact synergistically to lower blood pressure.

The S-nitrosothiols of the present invention facilitate and mediate acute lowering of blood pressure on administration to animals. The longer-term effects of ACE inhibition promote lower mean blood pressures once acute administration is discontinued. The new unique properties of this class of compounds are eminently suitable for the treatment of Reynauds syndrome, scleroderma, toxemia of pregnancy, acute renal failure, diabetic nephropathy, renal artery stenosis, acute myocardial infarction, left ventricular dysfunction without overt heart failure, angina pectoris, congestive heart failure, and hypertension, in particular, pulmonary hypertension.

The compounds of the present invention also have the added benefit that they do not induce tolerance to its direct vasodilatory effect as do organic nitrates (e.g., glyceryl trinitrate) since the nitrous oxide moiety is provided as part of an active complex with a thiol group thereby facilitating directly guanylate cyclase activation and smooth muscle relaxation. The compounds of the present invention are also relatively coronary selective, which provides an additional benefit to patients with coronary disease Moreover, the antiplatelet effects are unique and useful in the management of unstable angina, transient ischemic attacks, and hypercoagulable states.

The compounds having the structure represented by Formulae I and II may be prepared by various methods of synthesis. For general methods of synthesizing the free mercaptan precursor to the S-nitroso derivatives of the invention, see U.S. Pat. No. 4,154,960 incorporated herein by reference.

For example, the α-amino acyl derivative of the formula (III):

(III)

wherein A, B and R are defined above, is acylated with an acid of the formula (IV):

(IV)

wherein n and $R^3$ have the meaning defined above and $R^4$ is lower $C_1$–$C_4$ alkyl, by any of the known procedures for preparing dipeptides. For example, the carboxy group may be activated by formation of a mixed anhydride, symmetrical anhydride, acid chloride, active ester such as with N-hydroxysuccinamide and DCC, Woodward reagent K, N,N'-carbonylbisimidazole, EEDQ (N-ethoxycarbonyl-2-ethoxy-1,2-dihydroquinone) or the like. When R is lower $C_1$–$C_4$ alkoxy, this or other known methods of coupling such moieties can be used [For a review of these methods, see Methoden de Organischen Chemie (Houben-Weyl), Vol. XV, parts 1 and 2 (1974)]. The product of this reaction is a compound having the formula (V):

(V)

The compounds of Formula IV, wherein n is 1, may be obtained by displacement of the halo group from a carboxylic acid derivative having the formula (VI):

(VI)

wherein X is halogen, preferably chlorine or bromine, with the thiol acid $R^4$-COSH, wherein $R^4$ is as defined above.

The acyl group ($R^4$-CO) of formula V is then cleaved by ammonolysis to give the thiol of the formula (VII):

(VII)

Nitrosylation of the thiol group with $NaNO_2$ under acidic conditions (pH = 1 to 5) gives the S-nitroso derivative. Acids which may be used for this purpose include aqueous sulfuric, acetic and hydrochloric acids.

According to a preferred method of preparing S-nitroso proline derivatives of the invention, an α-amino acyl derivative of the Formula (VIII)

(VIII)

wherein m, $R^1$ and $R^2$ are defined above, is acylated with a haloalkanoic acid of the Formula (IX):

(IX)

wherein $R^1$, $R^3$ and n are defined above and X is a halogen, preferably chlorine or bromine. The amide linkage between the carboxy group of IX and the amino group of VIII may be prepared by any of the above-described procedures for the preparation of the dipeptides which are known to those skilled in the art. The product of this reaction is a compound of the formula (X):

(X)

This product (X) is then subjected to a displacement reaction with a thiolacid of the general formula (XI):

(XI)

wherein $R^4$ is lower $C_1$–$C_4$ alkyl, under basic conditions to give a product of the general Formula (XII):

(XII)

This compound, in which the thiol group is protected by the acyl group $R^4$CO-, is then converted to the thiol (XIII)

(XIII)

by ammonolysis.

It is understood that if $R^2$ is hydroxy, it may also be protected by any conventional hydroxy protecting group including, but not limited to, acyl, trialkylsilyl, dialkylarylsilyl, or tetrahydropyranyl. Nitrosylation of the thiol with $NaNO_2$ under acidic conditions (pH = 1 to 5), as described above, gives the S-nitroso derivative.

Alternatively, the compounds of Formula II wherein n is 1 can be synthesized by addition of a thiol acid across the double bond of an acrylate derivative of the Formula XIV to give Formula XII.

(XIV)

-continued (XII)

The acyl moiety (R⁴CO-) of Formula XII may then be cleaved by ammonolysis. Compounds represented by Formula XIV may be obtained by acylation of the amino group of Formula VIII with an acrylate acid of the Formula XV.

(XV)

The carboxylate group of Formula XV may be activated with a conventional activating group, such as those mentioned above, before condensation with VIII.

The compositions of the present invention may be administered by any means that effect vasodilation and platelet aggregation inhibition and thereby relieve the symptoms of angina pectoris, congestive heart failure, and hypertension. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the S-nitroso compound is contained in an amount effective to achieve its intended purpose. While individual needs vary, determination of optimal ranges of effective amounts of each component is with the skill of the art. Typical dosage forms contain 1 pmole/kg to 10 mmole/kg animal of the S-nitrosothiol derivative, or an equivalent amount of the pharmaceutically acceptable salt thereof.

Administration of the compounds of the invention, for example, S-nitrosocaptopril, is desirably effected in from 1 mcg to 300 mg dosage units daily, depending on the mode of administration, preferably by oral or intravenous administration. The compounds may be administered from 1 to 4 times daily or by continuous intravenous infusion.

In addition to the pharmacologically active compounds, the new pharmaceutical preparations may contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 5 percent, preferably from about 0.1 to 0.5 percent of active compound(s), together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as binders such as starch, paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or algenic acid or a salt thereof, such as sodium alginate. Auxiliaries are, above all, flow-regulating agents and lubricants, for example, silica, talc, steric acid or salts thereof, such as magnesium stearate or calcium stearate, and/or polyethylene glycol. Dragee cores are provided with suitable coatings which, if desired, are resistant to gastric juices. For this purpose, concentrated sugar solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES

Example 1: Preparation of S-Nitrosocaptopril

Typical preparations of S-nitrosocaptopril involve the reaction of 50 mM captopril with 50 mM $NaNO_2$ in 0.1 N acetic or sulfuric acid at room temperature for five minutes, after which the reaction solution is passed over a cation exchange resin, e.g., Dowex 50 in the protonated form, and the product eluted with water. The fractions that give positive reactions with N-(1-naphthyl)ethylenediamine, after exposure to 0.15% $HgCl_2$ and diazotization with sulfanilamide, are lyophilized. Hygroscopic, bright red crystals were obtained that were shown to be S-nitrosocaptopril by NMR in deuterated DMSO and by mass spectroscopy. A visible absorption maximum exists at 546 nm with a shoulder at 513 nm.

Example 2: The Effect of S-Nitrosocaptopril on Arterial Tone

Figure 1:
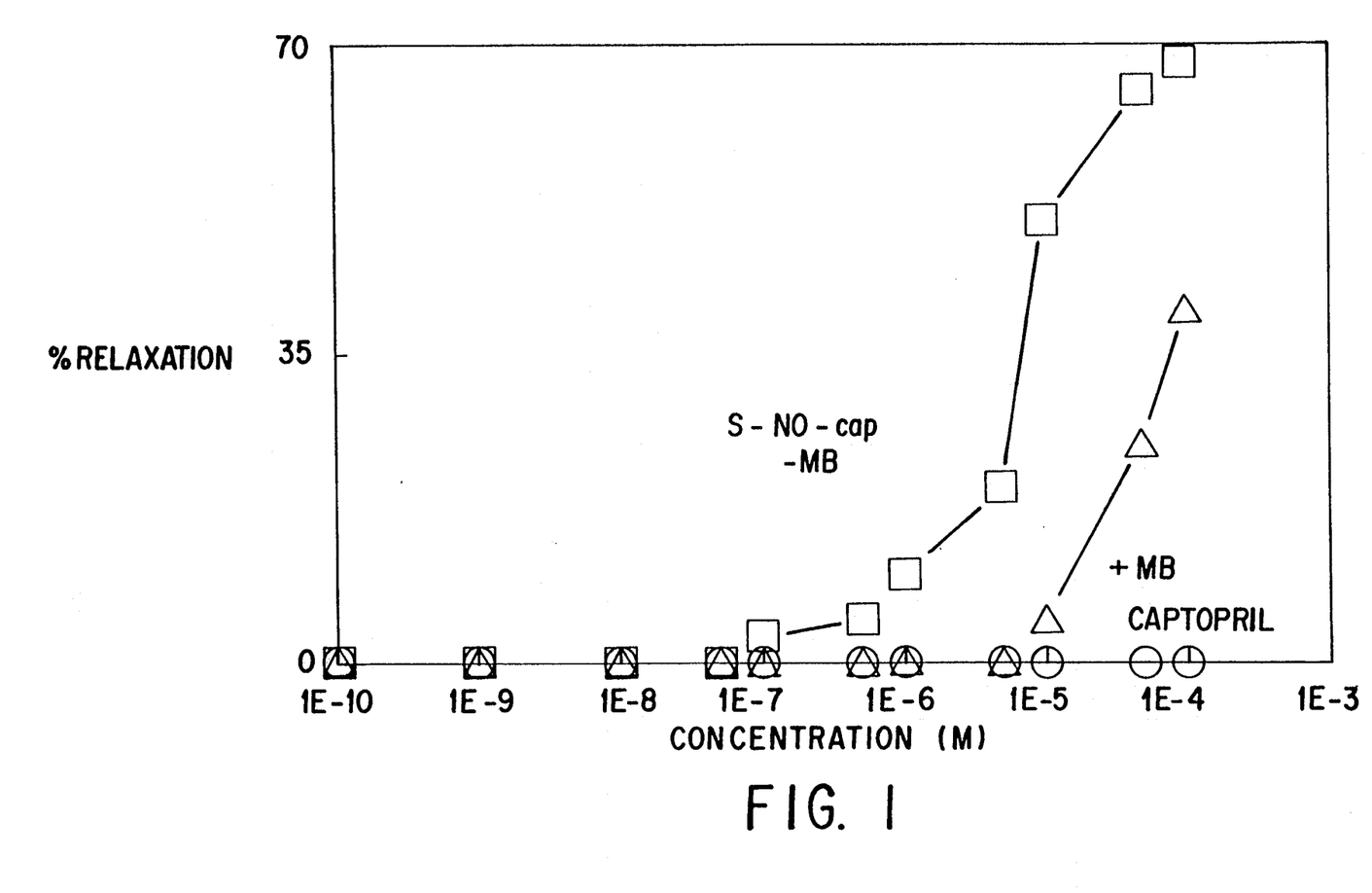
FIG. 1 depicts a graph of the % relaxation (tone) of canine femoral arteries contracted by norepinephrine for various concentrations of S-nitrosocaptopril (squares), methylene blue and S-nitrocaptopril (triangles), or captopril (circles).

Canine femoral arteries were freshly obtained and incubated in oxygenated, physiologic buffer, after which maximal contraction was induced by norephinephrine or KCl (see FIG. 1). Increasing concentrations of S-nitrosocaptopril (squares), S-nitrosocaptopril with the nitrate inhibitor methylene blue (triangles), or captopril (circles) were then incubated with the precontracted arterial rings and the reduction in tone monitored. Expressed as percent relaxation from maximal contraction, the data in FIG. 1 show clearly that S-nitrosocaptopril—in distinct contrast to captopril—is a potent direct vasodilator, the effect of which is partly inhibited by methylene blue, as is that of organic nitrates.

Figure 2:
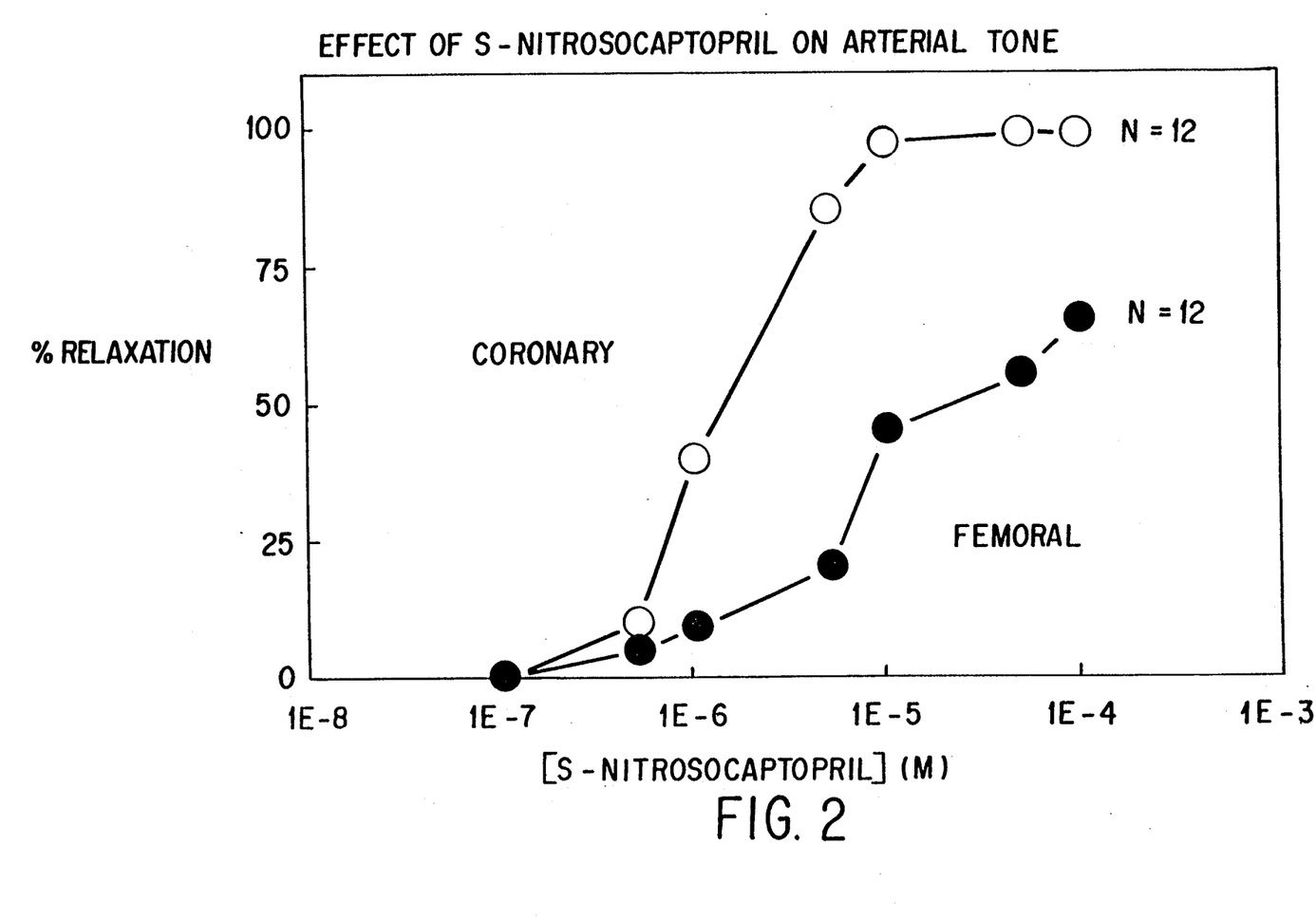
FIG. 2 depicts a graph of the % relaxation (tone) of canine femoral arteries contracted by norepinephrine (closed circles) or coronary arteries contracted by KCl (open circles) for various concentrations of S-nitrosocaptopril.

Example 3: Demonstration of the Relative Coronary Selectivity of S-Nitrosocaptopril Canine femoral (closed circles; see FIG. 2) or coronary (open circles) arteries were precontracted with norepinephrine or KCl and incubated with increasing concentrations of S-nitrosocaptopril. Reduction in tone was monitored and recorded as percentage relaxation. As shown in FIG. 2, S-nitrosocaptopril is more potent in the coronary than in the peripheral arterial bed.

Figure 3:
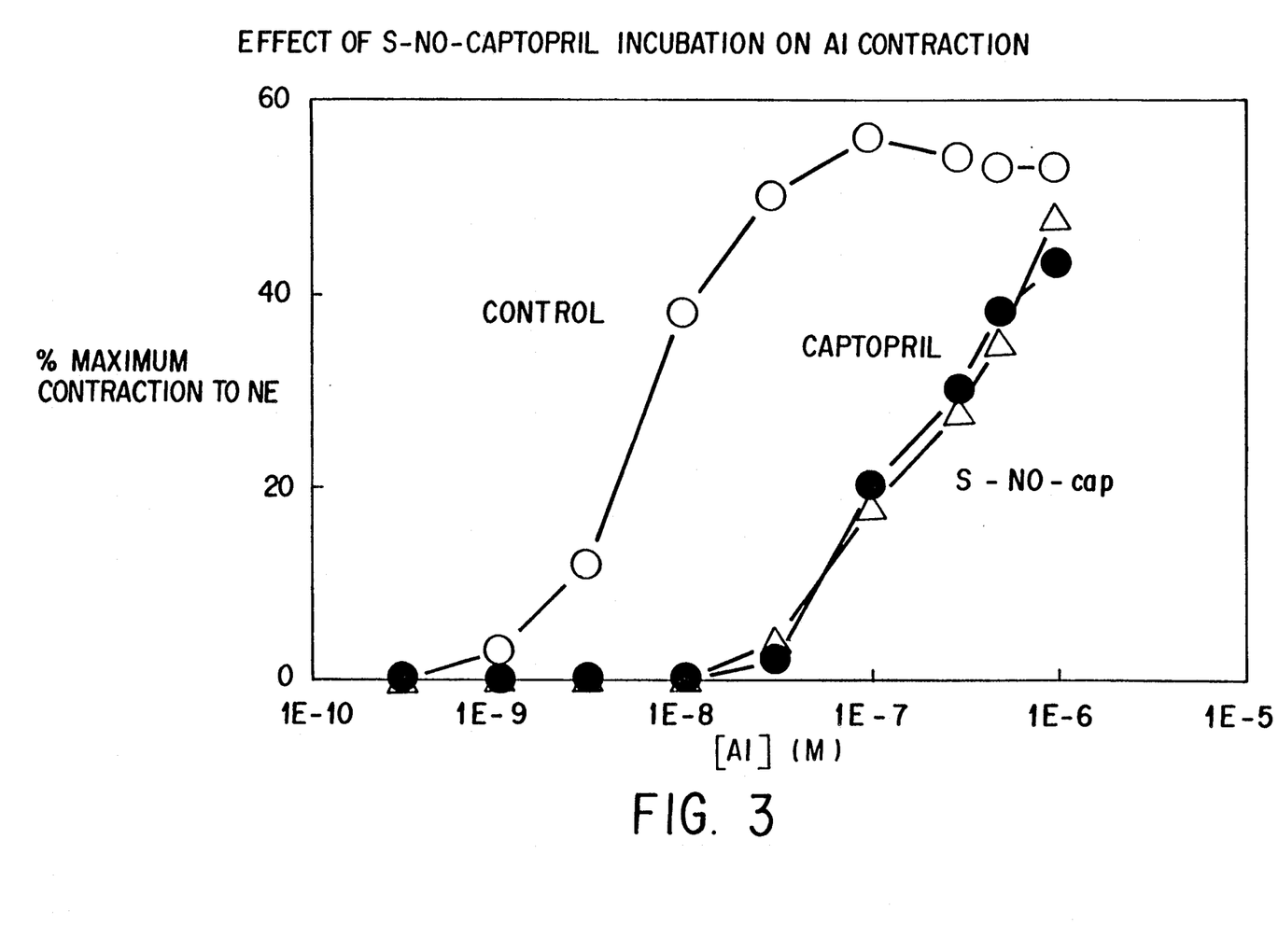
FIG. 3 depicts a graph of the % maximum contraction in response to increasing concentrations of angiotensin I for canine femoral arteries incubated with buffer (open circles), captopril (closed circles) or S-nitrosocaptopril (open triangles).

Example 4: The ACE Inhibiting Effect of S-Nitrosocaptopril in Canine Femoral Arteries Canine femoral arteries were incubated with buffer (open circles; see FIG. 3), captopril (closed circles), or S-nitrosocaptopril (open triangles) after which they were exposed to increasing concentrations of angiotension I and the percentage maximal contraction recorded. As shown in FIG. 3, the potent vasoconstrictor effect of angiotension I (a result of its conversion to angiotensin II) is markedly abrogated by captopril and, equivalently, by S-nitrosocaptopril.

Example 5: The Inhibitory Effect of S-Nitrosocaptopril on Platelet Aggregation Induced by ADP

Figure 4:
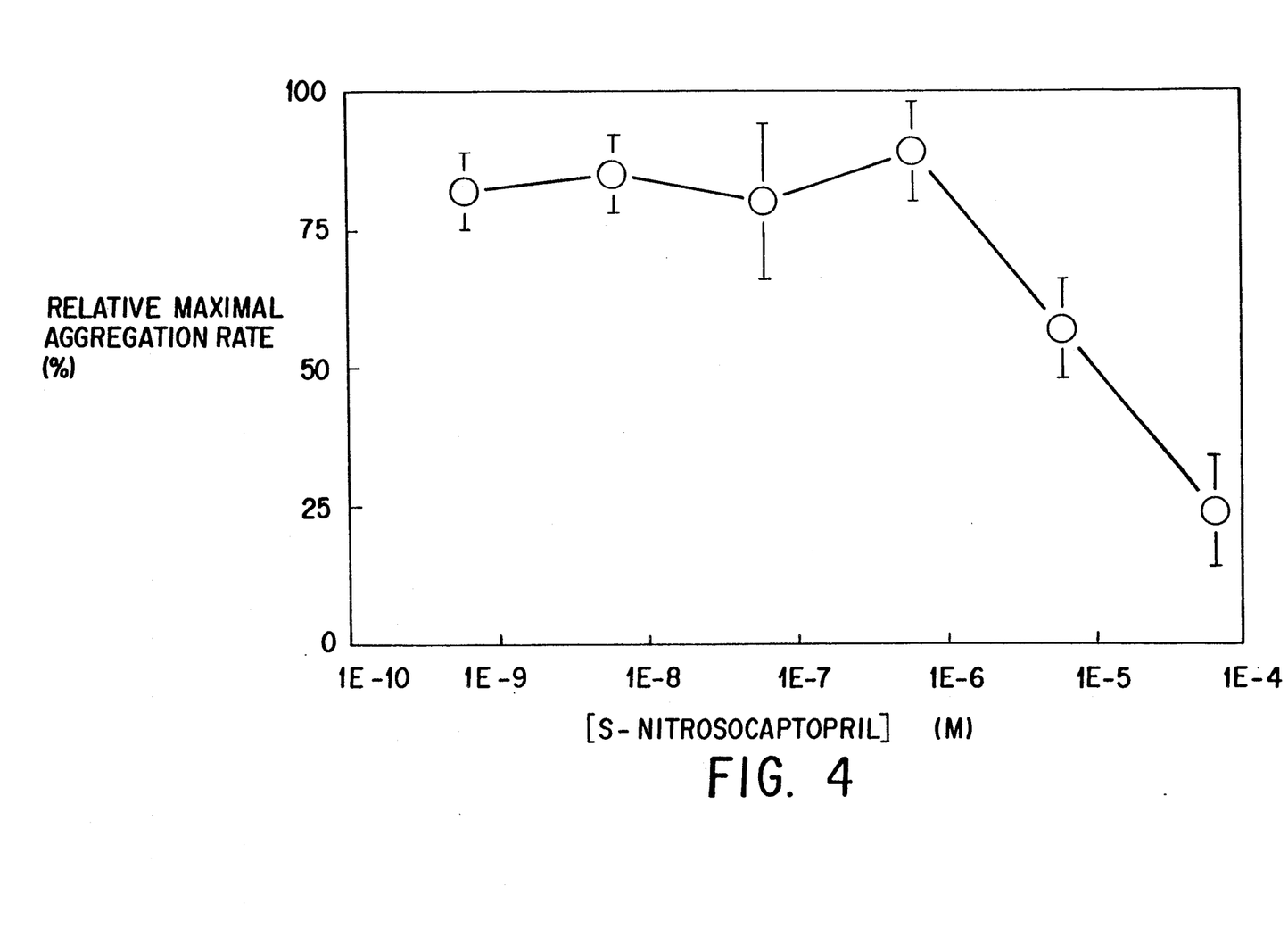
FIG. 4 depicts a graph of the relative maximal aggregation rate (%) of human platelets for increasing concentrations of S-nitrosocaptopril.

Human platelets in plasma were incubated with increasing concentrations of S-nitrosocaptopril, after which platelet aggregation was induced by 11 uM ADP. The rate of change of light scattering was recorded and plotted relative to that in the absence of S-nitrosocaptopril. As shown in FIG. 4, there is a significant attenuation of the aggregation response.

Figure 5:
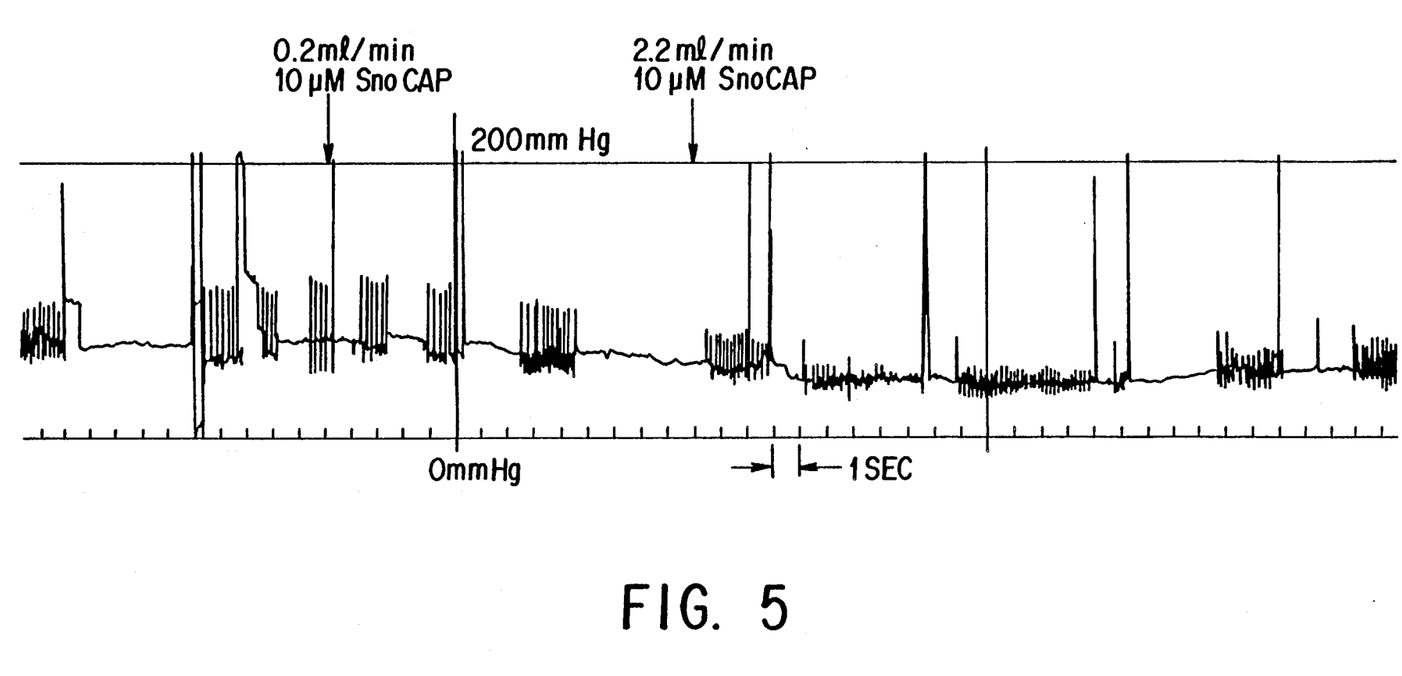
FIG. 5 depicts a strip chart record showing the effect of the administration of S-nitrosocaptopril to anesthetized rabbits.

Example 6: The Acute Effect of S-Nitrocaptopril on Arterial Pressure in the Anesthetized Rabbit A 1 nM solution of S-nitrocaptopril was infused in an ear vein of the rabbit at rates from 0.02 to 2.2 ml/min and the phasic and mean arterial pressure recorded in the femoral artery. As shown in FIG. 5, a clear decrease in blood pressure occurred upon administration of S-nitrosocaptopril. Solutions of captopril and $NaNO_2$ at the same concentration, and infused at the same rate, had no effect on blood pressure.

What is claimed is:

1. A pharmaceutical composition, comprising:
   (a) a therapeutically effective amount of a compound having the formula:

wherein
R is hydroxy, $NH_2$, $NHR^4$, $NR^4R^5$, or $C_1$–$C_7$ alkoxy, wherein $R^4$ and $R^5$ are $C_1$–$C_4$ alkyl, phenyl, or $C_1$–$C_4$ alkyl substituted by phenyl;

$R^1$ is hydrogen, $C_1$–$C_7$ alkyl, or $C_1$–$C_7$ alkyl substituted by phenyl, amino, guanidino, $NHR^6$ or $NR^6R^7$, wherein $R^6$ and $R^7$ are methyl or $C_1$–$C_4$ alkanoyl;

$R^2$ is hydrogen, hydroxy, $C_1$–$C_4$ alkoxy, phenoxy, or $C_1$–$C_7$ alkyl;

$R^3$ is hydrogen, $C_1$–$C_4$ alkyl or $C_1$–$C_7$ alkyl substituted by phenyl;

m is 2;

n is 0 to 2; and

(b) a pharmaceutically acceptable carrier.

2. The pharmaceutical composition of claim 1, wherein said compound is S-nitrosocaptopril.

3. A compound selected from the group consisting of N-acetyl-S-nitroso-D-cysteinyl-L-proline, N-acetyl-S-nitroso-D,L-cysteinyl-L-proline, 1-(4-amino-2-S-nitroso)mercaptomethylbutanoyl)-L-proline, 1-[2-(S-nitroso)mercaptomethyl-6-(N-methyl-N-acetyl-amino)-hexanoyl]-L-proline, 1-[5-guanidino-2-(S-nitroso)mercaptomethylpentanoyl]-L-proline, 1-[5-amino-2-(S-nitroso)mercaptomethylpentanoyl]-4hydroxy-L-proline, 1-[5-guanidino-2-(S-nitroso)mercaptomethylpentanoyl]-4-hydroxy-L-proline, 1-[2-aminomethyl-3-(S-nitroso)-mercaptomethyl-pentanoyl]-L-proline, and S-nitroso-L-cysteinyl-L-proline.

4. A pharmaceutical composition comprising a therapeutically effective amount of the compound of claim 3 and a pharmaceutically acceptable carrier.

5. A method for treating a cardiovascular-renal disease, comprising administering to an animal in need of such treatment an effective amount of a compound having the formula:

wherein
R is hydroxy, NH$_2$, NHR$^4$, NR$^4$R$^5$, or C$_1$-C$_7$ alkoxy, wherein R$^4$ and R$^5$ are C$_1$-C$_4$ alkyl, phenyl, or C$_1$-C$_4$ alkyl substituted by phenyl;

R$^1$ is hydrogen, C$_1$-C$_7$ alkyl, or C$_1$-C$_7$ alkyl substituted by phenyl, amino, guanidino, NHR$^6$ or NR$^6$R$^7$, wherein R$^6$ and R$^7$ are methyl or C$_1$-C$_4$ alkanoyl;

R$^2$ is hydrogen, hydroxy, C$_1$-C$_4$ alkoxy, phenoxy, or C$_1$-C$_7$ alkyl;

R$^3$ is hydrogen, C$_1$-C$_4$ alkyl or C$_1$-C$_7$ alkyl substituted by phenyl;

m is 2; and n is 0 to 2.

6. A method for treating a cardiovascular-renal disease, comprising administering to an animal in need of such treatment an effective amount of a compound selected from the group consisting of N-acetyl-S-nitroso-D-cysteinyl-L-proline, N-acetyl-S-nitroso-D,L-cysteinyl-L-proline, 1-(4-amino-2-S-nitroso)mercaptomethylbutanoyl)-L-proline, 1-[2-hexanoyl]-L-proline, 1-[5-guanidino-2-(S-nitroso)mercaptomethyl-pentanoyl]-L-proline, 1-[5-amino-2-(S-nitroso)mercaptomethylpentanoyl]-4hydroxy-L-proline, 1-[5-guanidino-2-(S-nitroso)mercaptomethyl-pentanoyl]-4-hydroxy-L-proline, 1-[2-aminomethyl-3-(S-nitroso)-mercaptomethylpentanoyl]-L-proline, and S-nitroso-L-cysteinyl-L-proline.

7. A method for treating scleroderma, comprising administering to an animal in need of such treatment a therapeutically effective amount of a compound having the formula:

wherein
R is hydroxy, NH$_2$, NHR$^4$, NR$^4$R$^5$, or C$_1$-C$_7$ alkoxy, wherein R$^4$ and R$^5$ are C$_1$-C$_4$ alkyl, phenyl, or C$_1$-C$_4$ alkyl substituted by phenyl;

R$^1$ is hydrogen, C$_1$-C$_7$ alkyl, or C$_1$-C$_7$ alkyl substituted by phenyl, amino, guanidino, NHR$^6$ or NR$^6$R$^7$, wherein R$^6$ and R$^7$ are methyl or C$_1$-C$_4$ alkanoyl;

R$^2$ is hydrogen, hydroxy, C$_1$-C$_4$ alkoxy, phenoxy, or C$_1$-C$_7$ alkyl;

R$^3$ is hydrogen, C$_1$-C$_4$ alkyl or C$_1$-C$_7$ alkyl substituted by phenyl;

m is 2; and n is 0 to 2.

8. A method for treating scleroderma, comprising administering to an animal in need of such treatment a therapeutically effective amount of a compound selected from the group consisting of N-acetyl-S-nitroso-D-cysteinyl-L-proline, N-acetyl-S-nitroso-D,L-cysteinyl-L-proline, 1-(4-amino-2-nitroso)mercapto-methylbutanoyl)-L-proline, 1-[2-(S-nitroso)mercaptomethyl-6-(N-methyl-N-acetyl-amino)-hexanoyl]-L-proline, 1-[5-guanidino-2-(S-nitroso)mercaptomethylpentanoyl]-L-proline, 1-[5-amino-2-(S-nitroso)mercaptomethylpentanoyl]-4-hydroxy-L-proline, 1-[5-guanidino-2-(S-nitroso)mercaptomethyl-pentanoyl]-4-hydroxy-L-proline, 1-[2-aminomethyl-3-(S-nitroso)-mercaptomethyl-pentanoyl]-L-proline, and S-nitroso-L-cysteinyl-L-proline.

9. A method for treating toxemia of pregnancy, comprising administering to an animal in need of such treatment an effective amount of a compound having the formula:

wherein
R is hydroxy, NH$_2$, NHR$^4$, NR$^4$R$^5$, or C$_1$-C$_7$ alkoxy, wherein R$^4$ and R$^5$ are C$_1$-C$_4$ alkyl, phenyl, or C$_1$-C$_4$ are substituted by phenyl;

R$^1$ is hydrogen, C$_1$-C$_7$ alkyl, or C$_1$-C$_7$ alkyl substituted by phenyl, amino, guanidino, NHR$^6$ or NR$^6$R$^7$, wherein R$^6$ and R$^7$ are methyl or C$_1$-C$_4$ alkanoyl;

R$^2$ is hydrogen, hydroxy, C$_1$-C$_4$ alkoxy, phenoxy, or C$_1$-C$_7$ alkyl;

R$^3$ is hydrogen, C$_1$-C$_4$ alkyl or C$_1$-C$_7$ alkyl substituted by phenyl;

m is 2;

n is 0 to 2.

10. A method for treating toxemia or pregnancy, comprising administering to an animal in need of such treatment an effective amount of a compound selected from the group consisting of N-acetyl-S-nitroso-D-cysteinyl-L-proline, N-acetyl-S-nitroso-D,L-cysteinyl-L-proline, 1-(4-amino-2-S-nitroso)mercapto-methylbutanoyl)-L-proline, 1-[2-(S-nitroso)mercaptomethyl-6-(N-methyl-N-acetyl-amino)-hexanoyl]-L-proline, 1-[5-guanidino-2-(S-nitroso)mercaptomethylpentanoyl -L-proline, 1-[5-guanidino-2-(S-nitroso)mercaptomethyl-pentanoyl]-4-hydroxy-L-proline, 1-[2-aminomethyl-3-(S-nitroso)-mercaptomethylpentanoyl]-L-proline, and S-nitroso-L-cysteinyl-L-proline.

11. A method of inhibiting angiotensin converting enzyme and effecting vasodilation in an animal comprising administering to the animal an effective amount of a compound having the formula:

wherein
R is hydroxy, NH$_2$, NHR$^4$, NR$^4$R$^5$, or C$_1$-C$_7$ alkoxy, wherein R$^4$ and R$^5$ are C$_1$-C$_4$ alkyl, phenyl, or C$_1$-C$_4$ alkyl substituted by phenyl;

R$^1$ is hydrogen, C$_1$-C$_7$ alkyl, or C$_1$-C$_7$ alkyl substituted by phenyl, amino, guanidino, NHR$^6$ or NR$^6$R$^7$, wherein R$^6$ and R$^7$ are methyl or C$_1$-C$_4$ alkanoyl;

R$^2$ is hydrogen, hydroxy, C$_1$-C$_4$ alkoxy, phenoxy, or C$_1$-C$_7$ alkyl;

R$^3$ is hydrogen, C$_1$-C$_4$ alkyl or C$_1$-C$_7$ alkyl substituted by phenyl;

m is 2;

n is 0 to 2.

12. A method of inhibiting angiotensin converting enzyme and effecting vasodilation in an animal comprising administering to the animal a therapeutically effective amount of a compound selected from the group consisting of N-acetyl-S-nitroso-D-cysteinyl-L-proline, N-acetyl-S-nitroso-D,L-cysteinyl-L-proline, 1-4-amino-2-S-nitroso)mercaptomethylbutanoyl)-L-proline, 1-[2-(S-nitroso)mercaptomethyl-6-(N-methyl-N-acetyl-amino)-hexanoyl]-L-proline, 1-[5-guanidino -2-(S-nitroso) mercaptomethylpentanoyl]-L-proline, 1-[5-amino-2-(S-nitroso)mercaptomethylpentanoyl]-4-hydroxy-L-proline, 1-[-5-guanidino-2-(S-nitroso)mercaptomethylpentanoyl]-4-hydroxy-L-proline, 1-[2-aminomethyl-3-(S-nitroso)-mercaptomethyl-pentanoyl]-L-proline, and S-nitroso-L-cysteinyl-L-proline.

13. The method of any one of claims 5–12, wherein said compound is administered as part of a pharmaceutical composition comprising a pharmaceutically acceptable carrier.

14. The method of claim 13, wherein said pharmaceutical composition comprises, per unit dose, one picomole to ten millimole of said compound, which is administered one to four times daily.

15. The method of claim 13, wherein said pharmaceutical composition is int he form of an injectable solution which is administered by continuous intravenous infusion.

16. The method of any of claims 5–12, wherein said animal is a human.

17. The method of any one of claims 5, 7, 9 and 11, wherein said compound is S-nitrosocaptopril.

* * * * *

UNITED STATES PATENT AND TRADEMARK OFFICE
CERTIFICATE OF CORRECTION

PATENT NO. : 5,002,964

DATED : March 26, 1991

INVENTOR(S) : Joseph Loscalzo and John Cooke

It is certified that error appears in the above-identified patent and that said Letters Patent is hereby corrected as shown below:

ON THE TITLE PAGE:   Item [75]   should be listed as follows:

"Inventors:  Joseph Loscalzo, Dedham, Mass., and
John Cooke, Needham Heights, Mass."

Signed and Sealed this

Fifth Day of May, 1992

Attest:

DOUGLAS B. COMER

Attesting Officer

Acting Commissioner of Patents and Trademarks